(12) United States Patent
Boiten

(10) Patent No.: US 7,500,407 B2
(45) Date of Patent: Mar. 10, 2009

(54) TORQUE SENSOR

(75) Inventor: Herman Boiten, Göttingen (DE)

(73) Assignee: Otto Bock Healthcare IP GmbH & Co. KG (DE)

( * ) Notice: Subject to any disclaimer, the term of this patent is extended or adjusted under 35 U.S.C. 154(b) by 0 days.

(21) Appl. No.: 11/044,642

(22) Filed: Jan. 27, 2005

(65) Prior Publication Data

US 2005/0166685 A1    Aug. 4, 2005

(30) Foreign Application Priority Data

Jan. 29, 2004    (DE) .................. 10 2004 004 678

(51) Int. Cl.
*G01L 3/02* (2006.01)
(52) U.S. Cl. ................................. 73/862.191
(58) Field of Classification Search ............. 73/862.191
See application file for complete search history.

(56) References Cited

U.S. PATENT DOCUMENTS

| 4,202,208 | A | * | 5/1980 | Byrne, Jr. ................. 73/862.25 |
| 4,454,770 | A | * | 6/1984 | Kistler .................... 73/862.633 |
| 4,521,924 | A | * | 6/1985 | Jacobsen et al. .......... 623/20.11 |
| 5,181,425 | A | * | 1/1993 | Livingston ............... 73/862.08 |
| 5,197,488 | A | * | 3/1993 | Kovacevic ................ 600/595 |
| 5,223,776 | A | * | 6/1993 | Radke et al. ............. 318/568.1 |
| 5,323,866 | A | * | 6/1994 | Simard et al. ............ 180/6.28 |
| 5,335,674 | A | * | 8/1994 | Siegler ................... 600/595 |
| 5,754,425 | A | * | 5/1998 | Murakami ................. 700/40 |
| 5,886,260 | A | * | 3/1999 | Anderson et al. ......... 73/514.21 |
| 5,993,400 | A | * | 11/1999 | Rincoe et al. ............ 600/595 |
| 6,129,319 | A | * | 10/2000 | Metelski ................ 248/123.2 |
| 6,702,805 | B1 | * | 3/2004 | Stuart .................... 606/1 |
| 2002/0052663 | A1 | | 5/2002 | Herr et al. |
| 2003/0029247 | A1 | | 2/2003 | Biedermann et al. |
| 2005/0234562 | A1 | | 10/2005 | Okuda |

FOREIGN PATENT DOCUMENTS

| DE | 1-2 18-10 C1 | 12/2002 |
| EP | 1570817 B1 | 9/2005 |
| WO | WO 00/17617 | 9/1999 |

OTHER PUBLICATIONS

Article: *Measurement of Stresses in Three Orthogonal Directions at the Residual Limb-Prosthetic Socket Interface* by Sanders and Daly, 8434 IEEE Transactions on Rehabilitation Engineering 1 (Jun. 1993), No. 2, New York, U.S.

* cited by examiner

*Primary Examiner*—Max Noori
(74) *Attorney, Agent, or Firm*—Faegre & Benson, LLP

(57) ABSTRACT

A torque sensor for measuring a torque at a predetermined location of a structural element, in particular of a prosthesis, can be arranged outside the measurement location by virtue of the fact that it is constructed as a sensor structure (13, 13', 23) that forms a virtual pivot axis (16, 16') outside the sensor. The sensor structure is provided with measurement transducers (29) which detect deformations of the sensor structure (13, 13', 23) and are used to determine a torque about the virtual pivot axis (16, 16'). A preferred application for the torque sensor is its incorporation in a prosthesis for the purpose of controlling an artificial joint.

19 Claims, 8 Drawing Sheets

TORQUE SENSOR

This patent application claims priority to and the benefit of Germany patent application number 10 2004 004 678.6, filed on Jan. 29, 2004, and entitled DREHMOMENTSENSOR.

TECHNICAL FIELD

The invention relates to a torque sensor for measuring a torque at a pre-determined location of a structural element, in particular of a prosthesis.

BACKGROUND OF THE INVENTION

The invention is thus concerned with measuring a torque at a defined location of a structural element in order either simply to obtain information about the torque occurring at said location and use this information for warning purposes, or to carry out controls using the information concerning the torque that occurs. It is known in principle to determine torque using suitable measuring elements, for example strain gages, which are applied at the sites where the torque occurs. In many cases, arranging a torque sensor at the measurement site entails considerable design disadvantages, meaning that less suitable design solutions are employed or that the measurement is carried out at another, less suitable location.

One example of this is the controlling of an artificial knee joint. Such artificial knee joints are provided with a high degree of damping in the stance phase in order to keep the joint stable in the stance phase. By contrast, when the knee joint is deliberately flexed, a low degree of damping must take effect. To control the damping, it is known to determine, in proximity to the knee joint, the torque occurring about the knee axis or near to the knee axis. However, since a knee extension moment of about the same order develops during bending of the knee joint, and also shortly before said bending of the knee joint, a clean divide between stance phase and swing phase is difficult to realize. The sensitivity of the control is adversely affected by this.

It is known that better differentiation between stance phase and swing phase is possible by determining a torque directly above the foot, in order to deliver a signal similar to the ankle moment. The arrangement of the sensor in the below-knee area, however, has the disadvantage that the below-knee tube of a modular below-knee prosthesis has to be specially designed, thus necessitating much more complex construction work. Moreover, prosthetic feet with an integrated tibia pylon cannot be used.

BRIEF SUMMARY OF THE INVENTION

The object of the present invention is therefore to design a torque sensor in such a way that structural disadvantages caused by its arrangement in the structural element are avoided or at least reduced.

According to the invention, this object is achieved by a torque sensor of the aforementioned type which is characterized by the fact that it is constructed as a sensor structure forming a virtual pivot axis outside the sensor. It is provided with measurement transducers which detect deformations of the sensor structure and are used to determine a torque about the virtual pivot axis.

The torque sensor according to the invention thus permits determination of a torque at a location lying outside the sensor structure and coinciding with the virtual pivot axis of the sensor structure. For this purpose, the torque sensor, for its deformation, has in principle one degree of freedom.

It is known, particularly in the field of prosthetics, to use multi-axis pivot hinges with a virtual pivot axis which lies outside the hinge and moves during the hinge action. Such a multi-axis structure is necessary, for example, for disarticulation amputees since, in this case, for structural reasons, a knee axis cannot be arranged at the anatomically correct site directly below the thigh stump. In addition, the migrating virtual axis can be used to increase the desired stance stability and support flexion during the swing phase.

The sensor structure according to the invention can be constructed in an analogous manner, but only a very slight rotation of the sensor structure about the virtual pivot axis is permitted. In other words, only a negligible shifting of the pivot axis upon loading is permitted. For this purpose, for example, the freely movable pivot axes of the multi-axis structure can be replaced by only slightly bendable elastic hinges.

Another suitable structure can be realized with two rigid and, if appropriate, approximately parallel bridges which are connected by means of two leaf springs forming an angle to one another. The intersection line of the planes included by the leaf springs thus forms the virtual pivot axis outside the sensor structure.

In all the embodiments, the torque about the virtual pivot axis can be determined by means of a suitable deformation of the sensor structure via suitable measurement transducers. Suitable measurement transducers can be force transducers, pressure transducers and/or displacement transducers. The use of strain gages is particularly suitable.

The torque sensor according to the invention can preferably be used to control the hinge action of a prosthesis. The sensor structure can, in particular, be arranged to control an artificial knee joint in the knee area and to measure the torque in the below-knee area of the prosthesis. Moreover, the invention does not preclude the possibility of determining a torque not just outside the sensor structure, but also outside the structural element, in order thereby to achieve improved control.

BRIEF DESCRIPTION OF THE SEVERAL VIEWS OF THE DRAWINGS

The invention will be explained in more detail below with reference to illustrative embodiments shown in the drawings, in which.

DETAILED DESCRIPTION OF THE INVENTION

Figure 1:
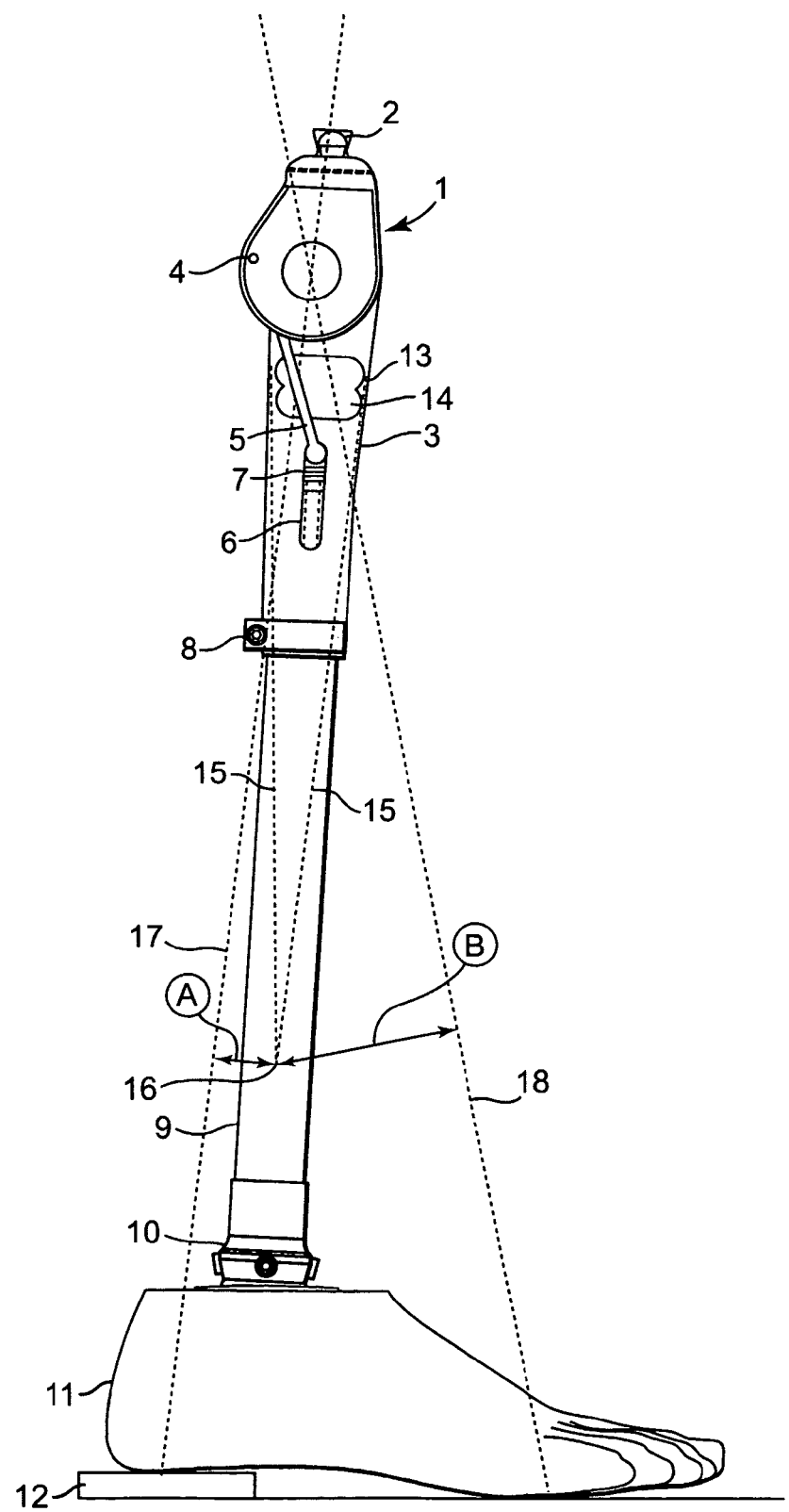
FIG. 1 shows a knee-joint prosthesis of modular construction with an artificial foot and with a torque sensor directly below the knee joint, which torque sensor has a virtual pivot axis intersecting the below-knee tube of the prosthesis.

The prosthesis shown in FIG. 1 has a mono-axial knee joint 1 which can be connected via an adapter 2 to a thigh prosthesis part (not shown). The knee joint 1 has, on its underside, a tube attachment 3 in which a rod 5 connected to an eccentric pivot pin 4 is mounted displaceably in a longitudinal guide 6 counter to the restoring force of a compression spring 7. Upon a flexion movement of the knee joint 1, the rod 5 is pushed downward counter to the force of the restoring spring 7 until the articulation of the auxiliary pin 4 overcomes a lower dead center. The restoring force of the compression spring 7 then supports the further flexion and stabilizes the knee in the flexed position when, for example, the prosthesis user has sat down.

The knee joint 1 is joined via a connecting sleeve 8 to a below-knee tube 9, the other end of which is connected to an adjustment collar 10 with adjustment pin of an artificial hingeless foot 11. To illustrate the position of use of the artificial foot 11, the latter is shown with the heel area placed on a small prop 12 which corresponds to the usual heel of a shoe.

A sensor structure 13 is fitted in the tube attachment 3 of the knee joint 1 below the pivot axis, the structure of which sensor structure 13 will be explained in more detail below. It can be seen from FIG. 1 that, because of a special inner contour 14 and its outer contour, the hollow sensor structure has four sites where the material is thinner and which thus function as elastic hinges. Vertical connection lines 15 of these hinges intersect in a virtual pivot axis 16 which, in the illustrative embodiment shown in FIG. 1, lies centrally in the below-knee tube 9 slightly above the ankle area.

FIG. 1 shows distances A, B of the virtual pivot axis 16 from force action lines 17, 18 which intersect the contact points of the foot 11 in the heel area and ball area, respectively, and extend through the pivot axis of the knee joint 1. The force action lines 17, 18 shown correspond roughly to the load situation of the prosthesis when the user stands on the heel 17 or, respectively, rolls the front part 18 of the foot forward.

Since the distance B to the force action line 18 for the front of the foot is considerably greater than the distance A to the force action line 17 for the heel, forces acting on the front of the foot are included in the torque measurement of the sensor 13 with greater leverage than the forces acting on the heel. Therefore, the sensor 13 shown in FIG. 1 is, as it were, primarily sensitive to the front area of the foot.

Figure 2:
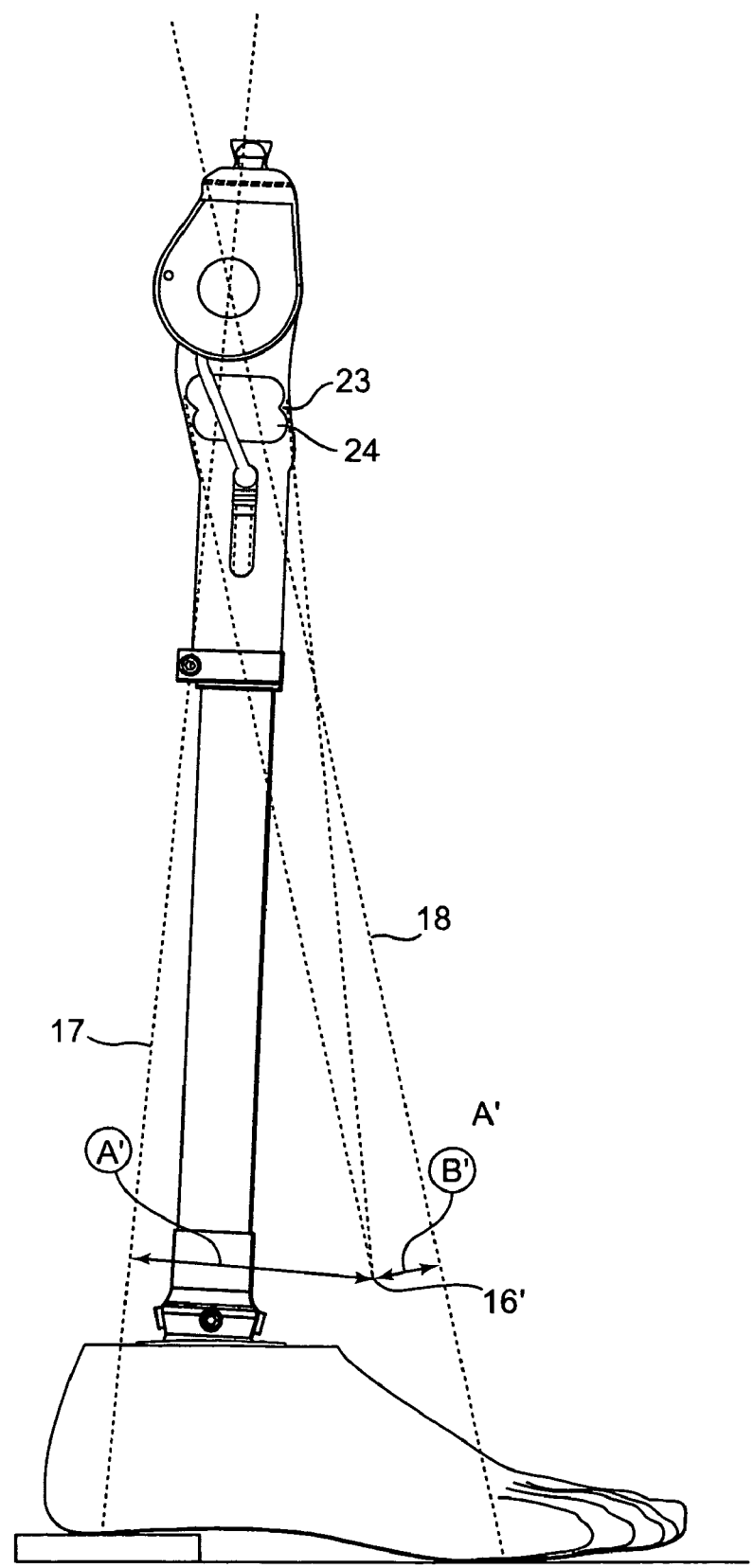
FIG. 2 shows an arrangement according to FIG. 1 with a torque sensor whose virtual pivot axis is arranged in the below-knee area outside the structural element, between the front area of the foot and the pivot axis of the knee joint.

The arrangement shown in FIG. 2 corresponds to that shown in FIG. 1, but with the difference that the sensor 23 shown, although fitted at the same site as the sensor 13 in FIG. 1, has a forwardly shifted virtual pivot axis 16' on account of the design of its inner contour 24 and outer contour. Thus, the distance A' of the virtual pivot axis 16' from the force action line 17 for the heel is considerably greater than the distance B' from the force action line 18 for the front of the foot. Accordingly, the sensor 23 shown in FIG. 2 is, as it were, sensitive to the heel. A suitable positioning of the virtual pivot axis 16, 16' facilitates the control carried out using the measurement data generated by the sensor 13.

Figure 3:
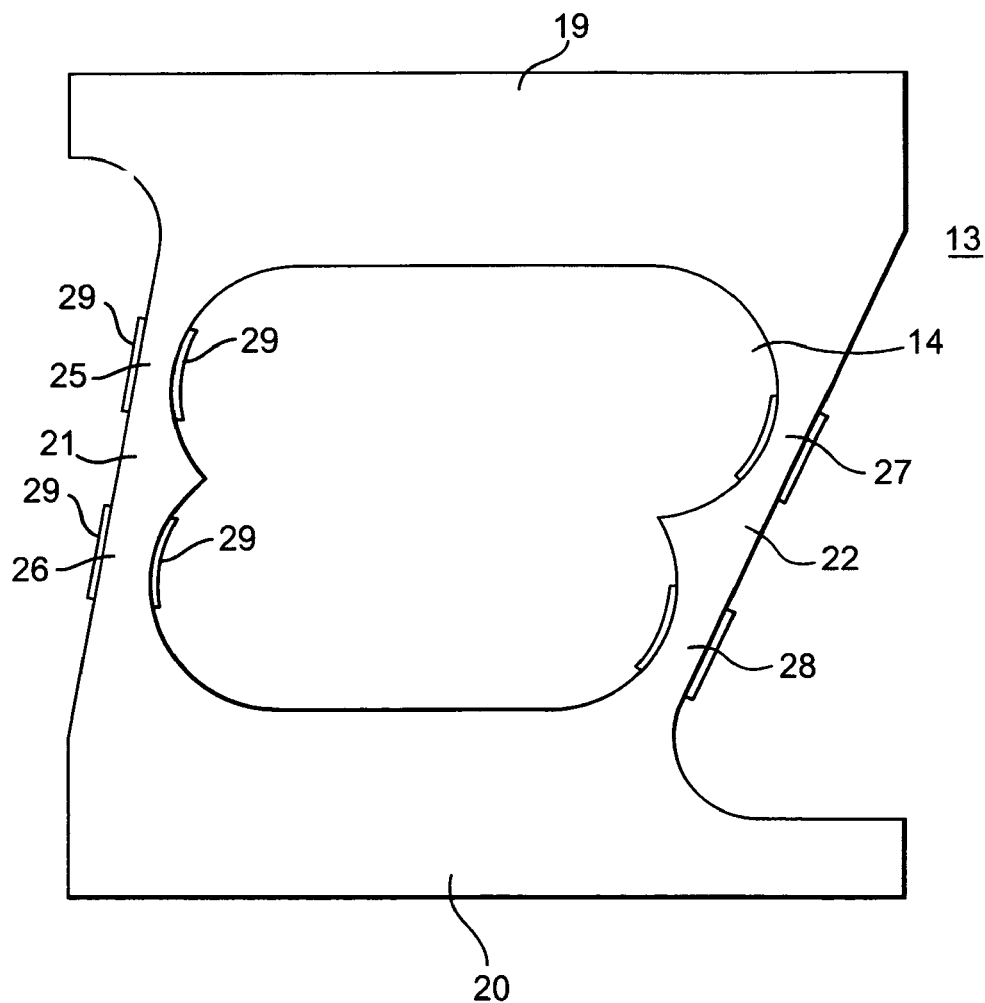
FIG. 3 shows a side view of a sensor that can be used in the arrangements according to FIG. 1 and FIG. 2.
Figure 4:
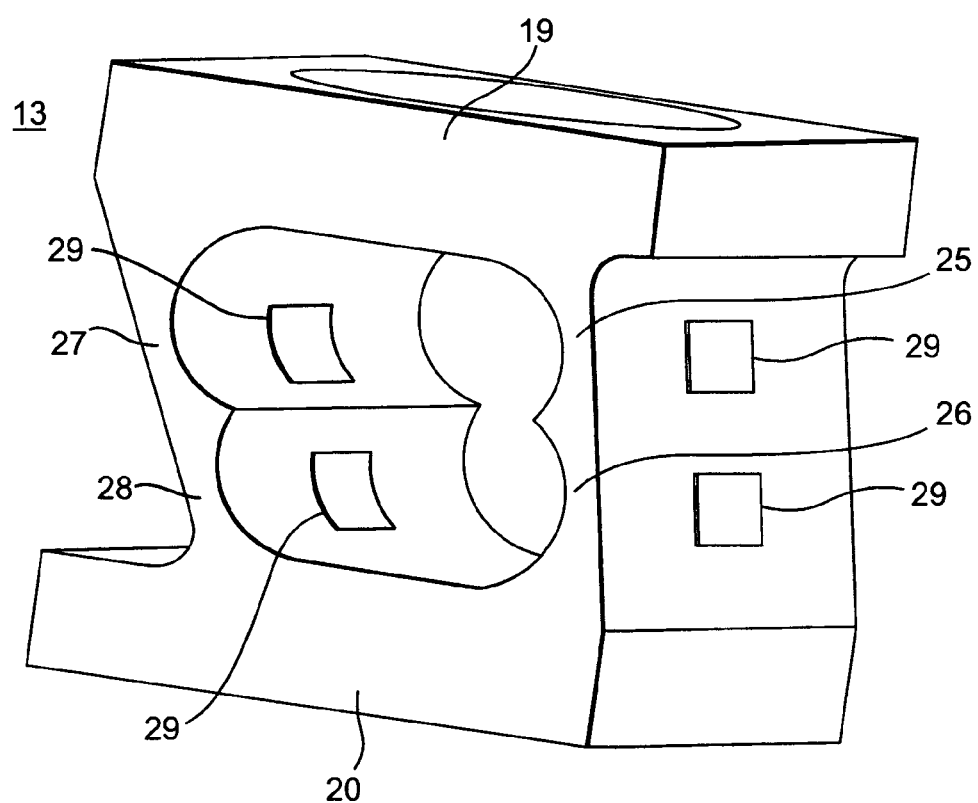
FIG. 4 shows a perspective view of the sensor according to FIG. 3.
Figure 5:
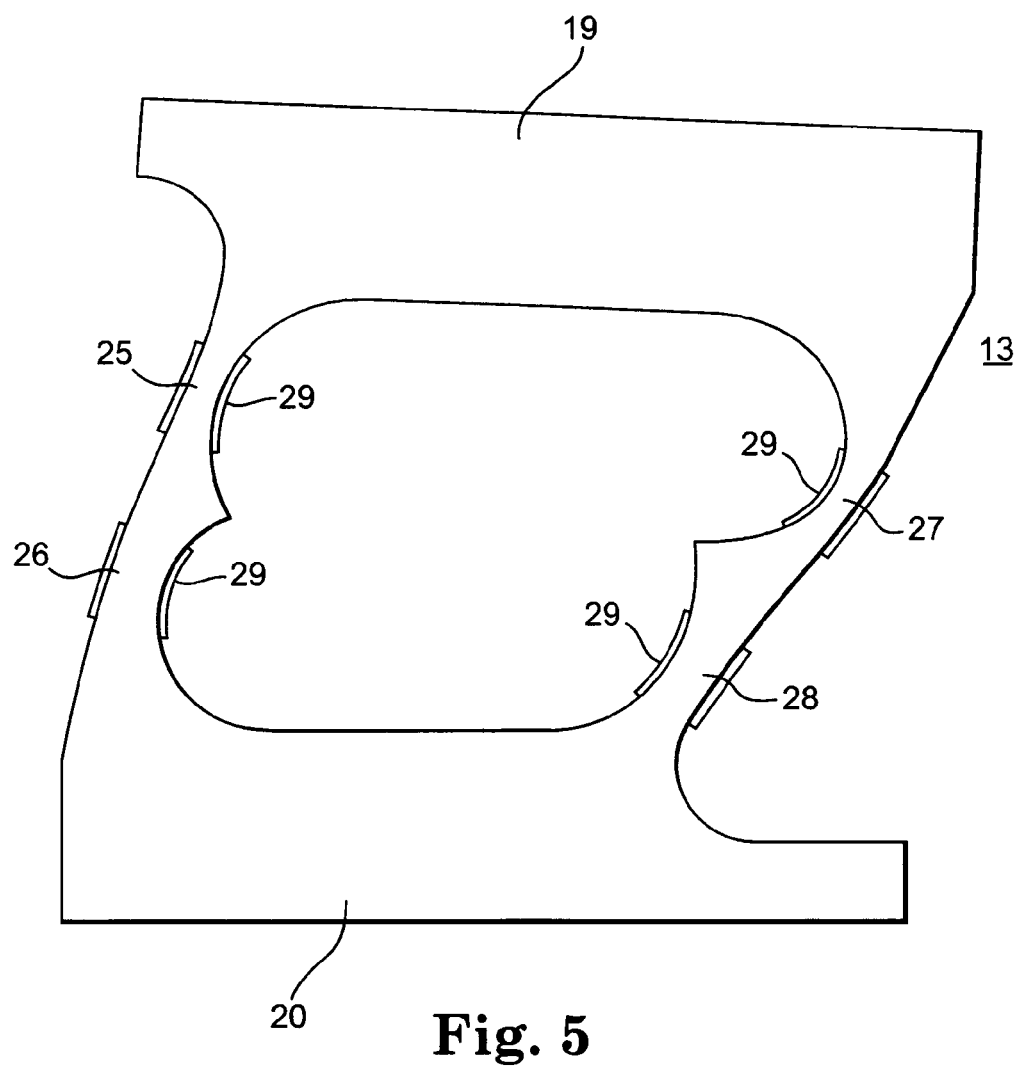
FIG. 5 shows a side view of the sensor according to FIG. 3 in a deformed state.

FIGS. 3 through 5 show a first embodiment of a sensor structure 13. This is composed of a block with a fixed upper bridge 19 and, parallel to this, a fixed lower bridge 20.

The interior 14 is delimited by two vertically extending bridges 21, 22 which form an angle to one another that corresponds to the angle of the connection lines 15 in FIG. 1. By virtue of the configuration of the inner contour 14 and outer contour, the bridges 21, 22 have four sites of minimal material thickness, which form four elastically deformable hinges 25, 26, 27, 28. Inner and outer strain gages 29 are arranged on both wall faces of each of the hinges 25, 26, 27, 28 and can be used to measure deformations of the elastically deformable hinges 25, 26, 27, 28.

FIG. 4 illustrates the above-described arrangement in a perspective view. It is clear from this that the strain gages 29 do not extend across the whole width of the hinges 25, 26, 27, 28 but instead have a much smaller width and are arranged centrally with respect to the depth of the sensor structure 13.

Compared to FIG. 3, FIG. 5 reveals a slight turning of the upper bridge 19 relative to the lower bridge 20. A turning of the upper bridge 19 occasioned by the torque about the virtual pivot axis 16 produces a corresponding turning of the elastic hinges 25, 26, 27, 28. The deformation measured by the strain gages 29 thus corresponds directly to a torque that occurs about the virtual pivot axis 16 of the sensor structure 13.

Figure 6:
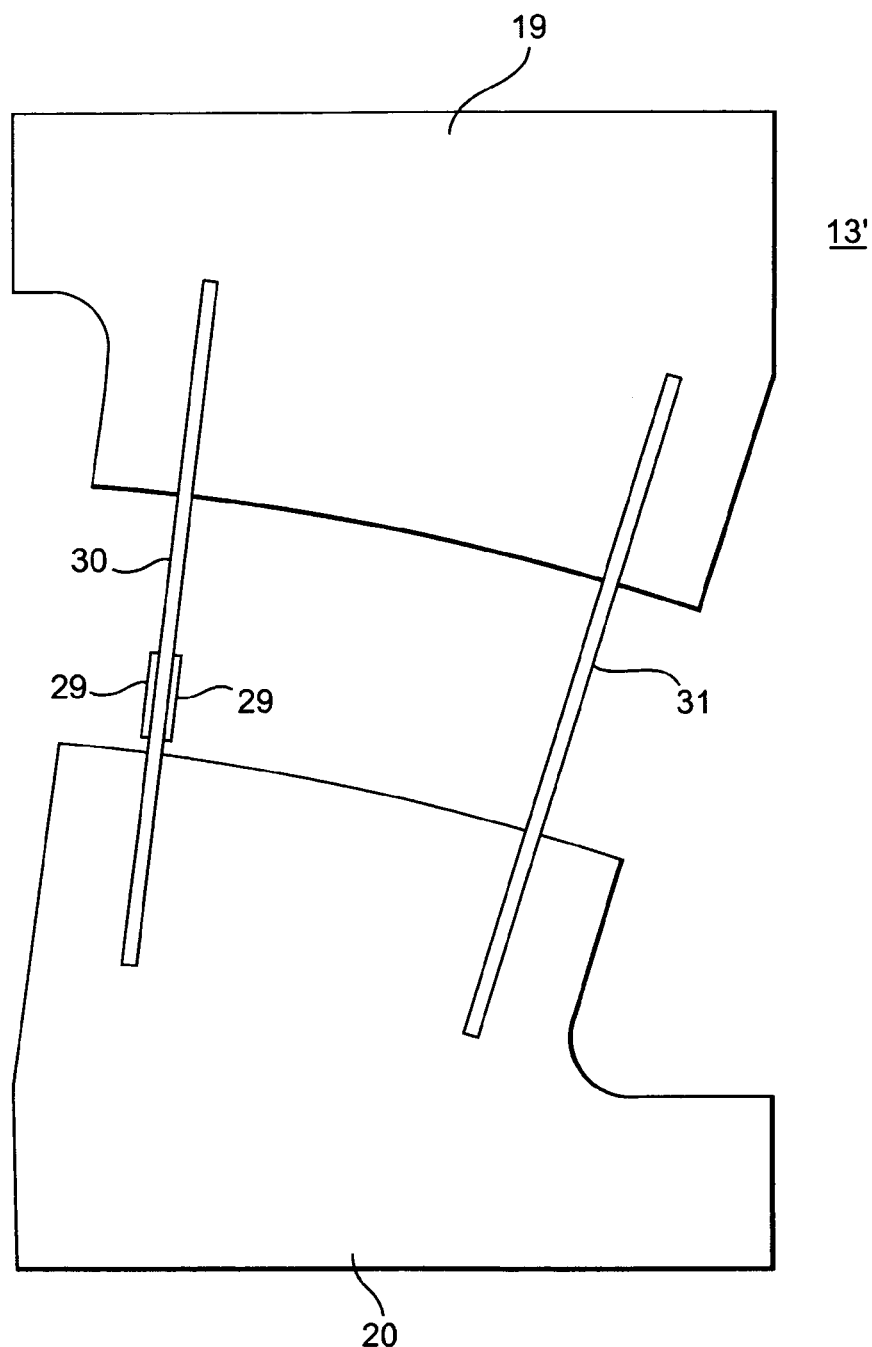
FIG. 6 shows a further embodiment of a torque sensor constructed with leaf springs.
Figure 7:
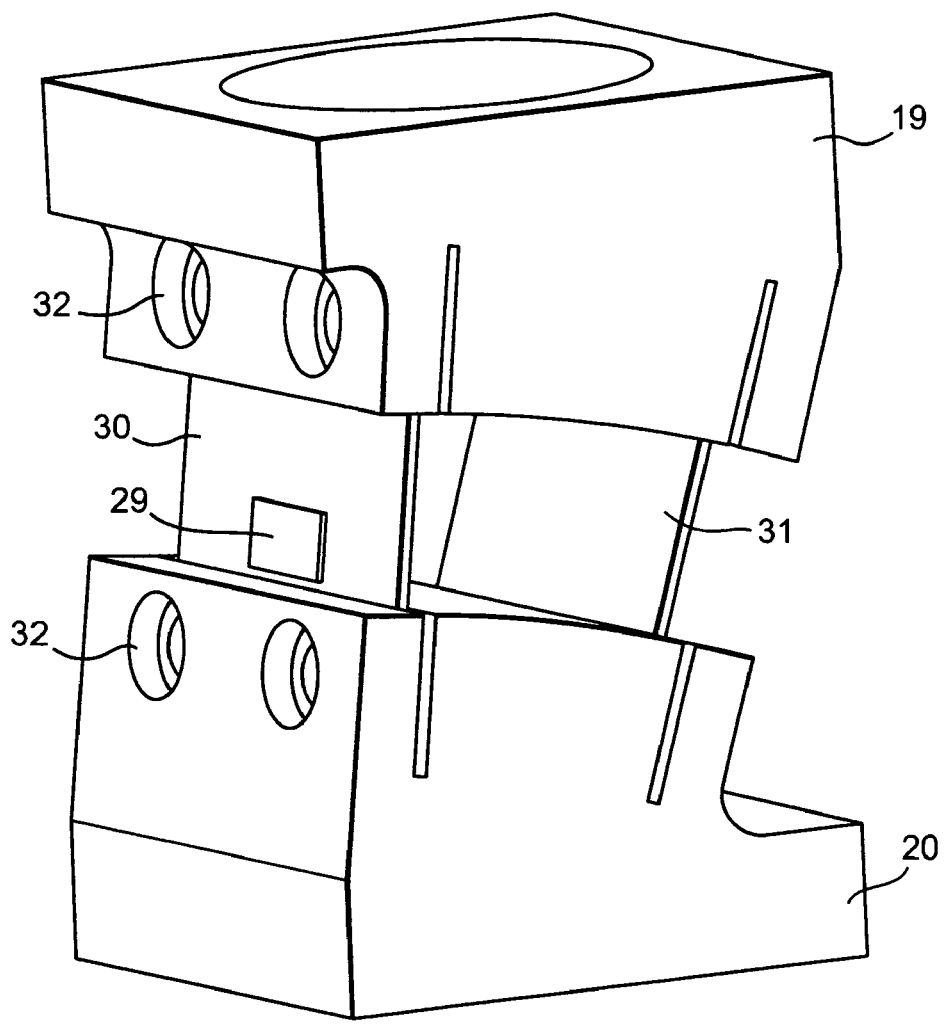
FIG. 7 shows a perspective view of the torque sensor according to FIG. 6.
Figure 8:
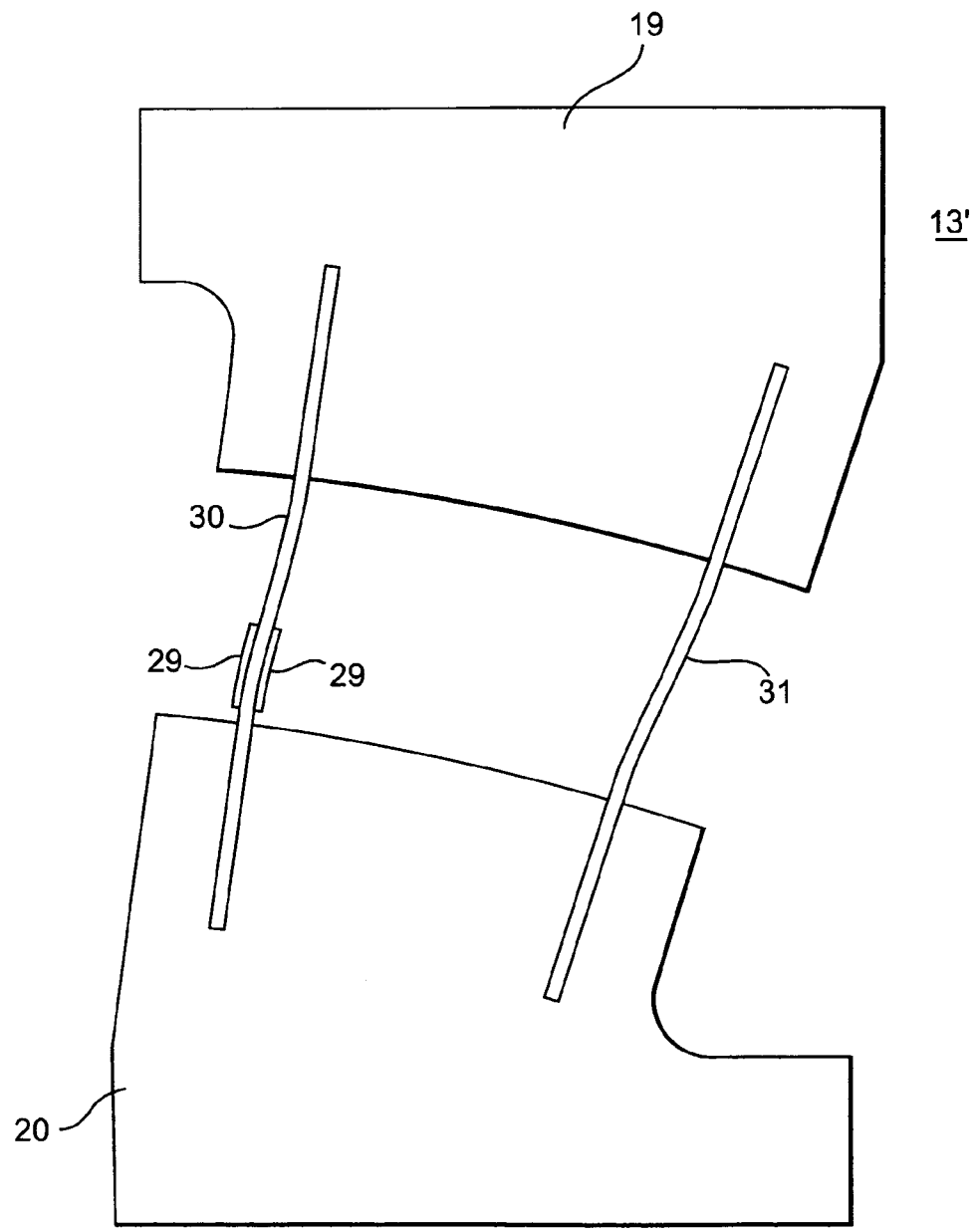
FIG. 8 shows a side view of the torque sensor in a deformed state.

FIGS. 6 through 8 show a further embodiment of a sensor structure 13' in which the upper bridge 19 and the lower bridge 20 are connected by means of two flat leaf springs 30, 31. The planes of the leaf springs 30, 31 correspond to the connection lines 15 and form an angle to one another whose intersection line defines the virtual pivot axis 16. In the illustrative embodiment shown, one leaf spring 30 is provided with inner and outer strain gages 29.

The perspective view according to FIG. 7 shows that the rigid bridges 19, 20 have holes 32 which serve to secure or clamp the leaf springs 30, 31. FIG. 8 shows a loaded state of the sensor structure 13' where, because of a torque in the virtual pivot axis 16, the leaf springs 30, 31 are deformed in each case by two bends, each with two bend points, as a result of which a slight turning of the upper rigid bridge 19 relative to the lower rigid bridge 20 takes place. The strain gages 29 detect the bending of the leaf spring 30 at one of the bend points of the leaf spring 30. This bending is in a direct relationship with the torque about the virtual pivot axis 16, 16' of the sensor structure 13. The bending at the other bend points too can be used to determine the torque about the virtual pivot axis. A combined measurement at several bend points may in some cases increase the accuracy of the measurement.

Whereas the embodiment of the sensor structure 13 according to FIGS. 3 through 5 can be seen clearly as a four-hinge structure, the embodiment according to FIGS. 6 through 8 shows that other structures are also suitable for the torque measurement according to the invention outside the sensor structure 13, 13', 23.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

What is claimed is:

1. A torque sensor for measuring a torque at a predetermined location with respect to a structural element, the torque sensor comprising:
    a sensor structure formed within the structural element, the sensor structure defining a virtual pivot axis at the predetermined location, wherein the predetermined location is located a distance from the sensor structure, the sensor structure including elastically deformable hinges and measurement transducers which detect deformations of the elastically deformable hinges to determine the torque about the virtual pivot axis.

2. The torque sensor as claimed in claim 1, wherein the sensor structure is designed as a four-hinge structure.

3. The torque sensor as claimed in claim 2, wherein the measurement transducers are strain gages.

4. A torque sensor for measuring a torque at a predetermined location with respect to a structural element, the torque sensor comprising:

a sensor structure formed within the structural element, the sensor structure defining a virtual pivot axis at the predetermined location, wherein the predetermined location is located a distance from the sensor structure, the sensor structure including two planar leaf-spring arrangements whose planes intersect in the virtual pivot axis and measurement transducers which detect deformations of the leaf spring elements to determine the torque about the virtual pivot axis.

5. The torque sensor as claimed in claim 1, wherein the measurement transducers are strain gages.

6. The torque sensor as claimed in claim 1, wherein the structural element comprises a prosthesis and the torque sensor is used to control an artificial joint of the prosthesis.

7. A prosthesis including an artificial joint formed with respect to a structural element, the prosthesis comprising:

a torque sensor adapted to control the artificial joint, the torque sensor formed within the structural element and configured to measure a torque at a predetermined location with respect to the structural element, the torque sensor including a sensor structure defining a virtual pivot axis located at the predetermined location, wherein the predetermined location is located a distance from the sensor structure, the sensor structure including measurement transducers which detect deformations of the sensor structure and are used to determine the torque about the virtual pivot axis.

8. The prosthesis as claimed in claim 7, wherein the torque sensor is designed as a multi-hinge structure with elastically deformable hinges.

9. The prosthesis as claimed in claim 8, wherein the torque sensor is designed as a four-hinge structure.

10. The prosthesis as claimed in claim 7, wherein the torque sensor is designed with two planar leaf-spring arrangements whose planes intersect in the virtual pivot axis.

11. The prosthesis as claimed in claim 7, wherein the measurement transducers are strain gages.

12. The prosthesis as claimed in claim 7, wherein the artificial joint comprises a knee joint with the sensor structure provided in the knee area, and wherein the virtual pivot axis of the sensor structure lies in the below-knee area of the prosthesis.

13. The prosthesis as claimed in claim 12, wherein the virtual pivot axis of the sensor structure lies in the ankle area of the prosthesis.

14. A method of sensing torque for use in controlling an artificial joint of a prosthesis, the method comprising the steps of:

providing a torque sensor within a structural element of the prosthesis for measuring a torque at a predetermined location with respect to the prosthesis, the torque sensor including a sensor structure defining a virtual pivot axis located at the predetermined location, wherein the predetermined location is located a distance from the sensor structure;

detecting deformations of the sensor structure; and determining the torque about the virtual pivot axis based on the detected deformations, wherein the torque may be used to control the artificial joint.

15. The method of claim 14, wherein the step of detecting deformations comprises the step of providing measurement transducers on the sensor structure.

16. The method of claim 15, wherein the measurement transducers comprise strain gages.

17. The method of claim 14, wherein the sensor structure comprises a multi-hinged structure with elastically deformable hinges.

18. The method of claim 14, wherein the sensor structure comprises two planar leaf-spring arrangements whose planes intersect in the virtual pivot axis.

19. The torque sensor as claimed in claim 4, wherein the measurement transducers are strain gages.

* * * * *

UNITED STATES PATENT AND TRADEMARK OFFICE
CERTIFICATE OF CORRECTION

PATENT NO. : 7,500,407 B2  
APPLICATION NO. : 11/044642  
DATED : March 10, 2009  
INVENTOR(S) : Herman Boiten It is certified that error appears in the above-identified patent and that said Letters Patent is hereby corrected as shown below:

On title page Item (73) Assignee;
Delete "Otto Bock Healthcare IP GmbH & Co. KG" and insert --Otto Bock Healthcare GmbH--

Signed and Sealed this

Twelfth Day of January, 2010

David J. Kappos
*Director of the United States Patent and Trademark Office*